(12) United States Patent
Voudouris (10) Patent No.: US 7,214,057 B2
(45) Date of Patent: May 8, 2007

(54) SELF-LIGATING ORTHODONTIC BRACKET

(75) Inventor: John C. Voudouris, Toronto (CA)

(73) Assignee: Ceramic Sciences Incorporated, Toronto, Ontario (CA)

( * ) Notice: Subject to any disclaimer, the term of this patent is extended or adjusted under 35 U.S.C. 154(b) by 0 days.

(21) Appl. No.: 11/372,618

(22) Filed: Mar. 10, 2006

(65) Prior Publication Data

US 2006/0204918 A1    Sep. 14, 2006

Related U.S. Application Data

(60) Provisional application No. 60/729,916, filed on Oct. 25, 2005, provisional application No. 60/594,092, filed on Mar. 10, 2005.

(51) Int. Cl.
*A61C 7/00* (2006.01)
(52) U.S. Cl. .................................................. 433/11
(58) Field of Classification Search .................. 433/10, 433/11, 8, 13, 9
See application file for complete search history.

(56) References Cited

U.S. PATENT DOCUMENTS

| | | | |
|---|---|---|---|
| 3,772,787 A | 11/1973 | Hanson | |
| 3,871,096 A | 3/1975 | Wallshein | |
| 4,023,274 A | 5/1977 | Wallshein | |
| 4,144,642 A | 3/1979 | Wallshein | |
| 4,171,568 A | 10/1979 | Förster | |
| 4,197,642 A | 4/1980 | Wallshein | |
| 4,212,638 A * | 7/1980 | Korn ............................ | 433/8 |
| 4,248,588 A | 2/1981 | Hanson | |
| 4,386,909 A | 6/1983 | Hanson | |
| 4,443,189 A | 4/1984 | Wildman | |
| 4,492,573 A | 1/1985 | Hanson | |
| 4,655,708 A | 4/1987 | Fujita | |
| 4,786,252 A | 11/1988 | Fujita | |
| 4,819,316 A * | 4/1989 | Rossini et al. ........... | 29/896.11 |
| 5,094,614 A | 3/1992 | Wildman | |
| 5,269,680 A * | 12/1993 | Kawaguchi .................... | 433/9 |
| 5,380,197 A | 1/1995 | Hanson | |

(Continued)

FOREIGN PATENT DOCUMENTS

DE        202004017951        5/2005

(Continued)

OTHER PUBLICATIONS

International Search Report and Written Opinion issued on Jul. 4, 2006 for corresponding International Application No. PCT/CA2006/000347.

*Primary Examiner*—Melba Bumgarner
(74) *Attorney, Agent, or Firm*—Michael Best & Friedrich LLP (57) ABSTRACT

An orthodontic bracket assembly and method of assembling an orthodontic bracket assembly. The bracket assembly may generally include a base defining an archwire slot and having a lingual surface attachable to a tooth, the base defining a recess extending from the lingual surface, an insert positionable in the recess, a slot being at least partially defined by the insert, and a locking member including a lingual portion receivable in the slot to support the locking member on the base, the lingual portion being movable in the slot between an open position, in which the locking member permits access to the archwire slot, and a closed position, in which the locking member inhibits access to the archwire slot.

23 Claims, 10 Drawing Sheets

U.S. PATENT DOCUMENTS

| | | |
|---|---|---|
| 5,474,446 A | 12/1995 | Wildman et al. |
| 5,562,444 A | 10/1996 | Heiser et al. |
| 5,586,882 A | 12/1996 | Hanson |
| 5,613,850 A | 3/1997 | Wildman et al. |
| 5,630,715 A | 5/1997 | Voudouris |
| 5,630,716 A | 5/1997 | Hanson |
| 5,711,666 A | 1/1998 | Hanson |
| 5,906,486 A | 5/1999 | Hanson |
| 6,168,428 B1 | 1/2001 | Voudouris |
| 6,247,923 B1 | 6/2001 | Vashi |
| 6,368,105 B1 | 4/2002 | Voudouris et al. |
| 6,695,612 B2 | 2/2004 | Abels et al. |
| 6,942,483 B2 | 9/2005 | Heiser |
| 6,957,957 B2 | 10/2005 | Pospisil |

FOREIGN PATENT DOCUMENTS

| | | |
|---|---|---|
| DE | 202004017952 | 5/2005 |
| JP | 4180750 | 6/1992 |

* cited by examiner

SELF-LIGATING ORTHODONTIC BRACKET

RELATED APPLICATIONS

This patent application claims priority to prior-filed, co-pending U.S. Provisional Patent Application Serial Nos. 60/594,092, filed Mar. 10, 2005; and 60/729,916, filed Oct. 25, 2005; the entire contents of both of which are hereby incorporated by reference.

FIELD OF THE INVENTION

The present invention relates generally to the field of orthodontics and, more specifically, to the field of self-ligating orthodontic brackets.

BACKGROUND

According to established orthodontic techniques, it is well known to attach an orthodontic bracket to a patient's tooth. The bracket provides a location for attaching an arch wire and other orthodontic devices to facilitate movement of the tooth. According to established orthodontic techniques, it is well known to ligate an arch wire to the orthodontic bracket utilizing an elastic or metal ligature. In conventional orthodontic brackets, the ligature is wrapped around respective gingival and occlusal tie wings so as to overlay the arch wire at mesial and distal ends of the orthodontic bracket.

Typically, orthodontic brackets are made of a metallic material, such as stainless steel. These materials are commonly used because they are strong, non-staining, and relatively inexpensive. However, metallic materials can be cosmetically undesirable because they do not match the color of the patient's teeth, and thus the resulting brackets are very noticeable. To overcome the cosmetic difficulties noted above, manufacturers have developed brackets made from ceramic materials, such as monocrystalline or polycrystalline alumina. These materials can be developed to closely match or refract the color of the patient's teeth, thus resulting in a bracket that is less noticeable than common metal brackets.

Recently, designers have created self-ligating brackets that do not require a separate ligature for attachment of the arch wire to the bracket. One type of self-ligating bracket is supplied with a locking member that is movable between an open position, permitting access to the arch wire slot, and a closed position, inhibiting access to the arch wire slot. Self-ligating brackets substantially decrease the time involved in performing ligation procedures.

SUMMARY

The present invention provides a self-ligating orthodontic bracket assembly having a base and a locking member movable relative to the base. The base generally includes an opening (e.g., a gingival-occlusal opening extending all the way through the base on the lingual aspect), and the locking member includes a slide portion positioned in the opening and slidable relative to the base. The opening is formed at least partially by a slot in the lingual surface of the base.

In one embodiment, an insert may be positioned in the slot to define at least a portion of the opening. The insert can be a longitudinal member having a closed cross section (e.g., oval, rectangular, circular, etc.) or an open cross section (e.g., straight, L-shaped, C-shaped, etc.). When using an insert having a C-shaped cross section, the open side of the insert can be positioned to face the lingual surface of the base so that, when secured in place, the insert and base collectively define the opening extending through the base.

Independent features and independent advantages of the present invention will become apparent to those skilled in the art upon review of the following detailed description and drawings.

Before at least one embodiment of the invention is explained in detail, it is to be understood that the invention is not limited in its application to the details of construction and the arrangements of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting.

Although references are made below to directions, such as left, right, up, down, top, bottom, front, rear, forward, back, etc., in describing the drawings, they are made relative to the drawings (as normally viewed) for convenience. These directions are not intended to be taken literally or limit the present invention in any form.

DETAILED DESCRIPTION

Figure 1:
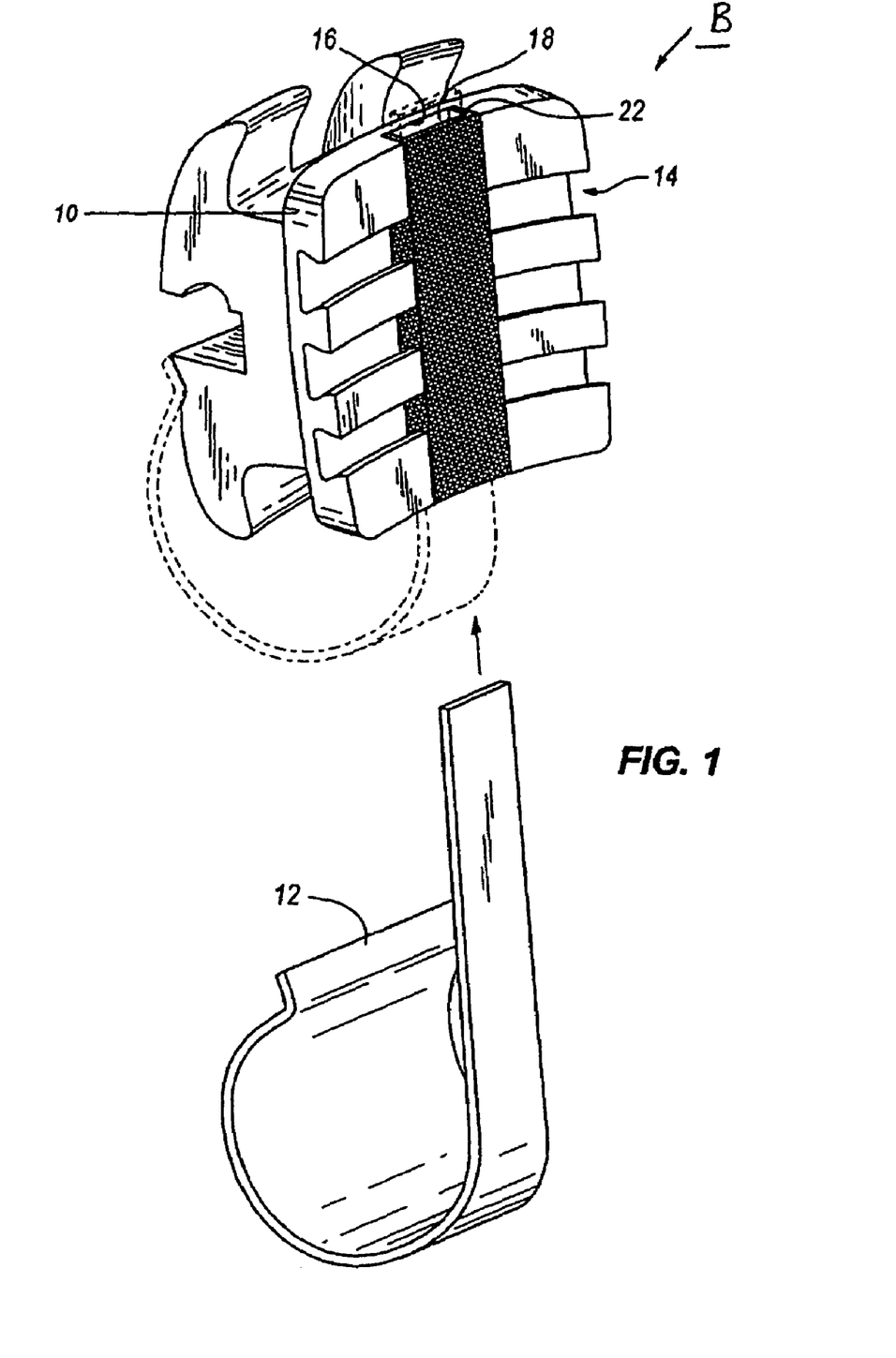
FIG. 1 is an exploded labial perspective view of an orthodontic bracket assembly embodying aspects of the present invention.
Figure 2:
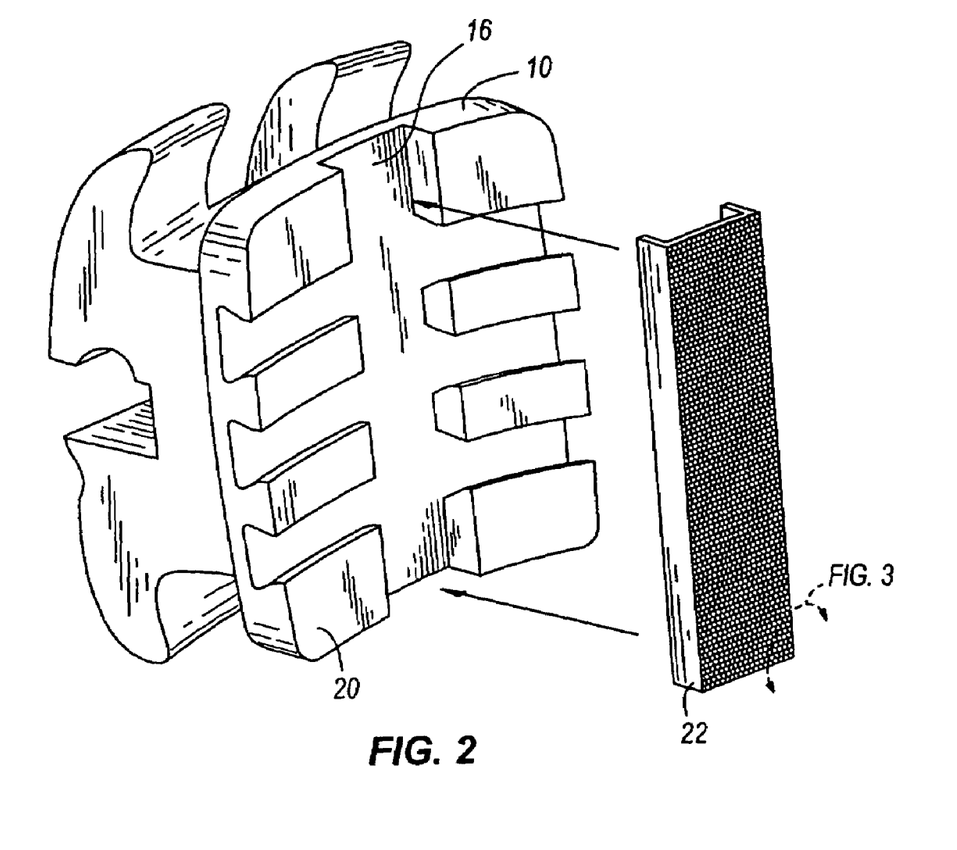
FIG. 2 illustrates an exploded lingual perspective view of the orthodontic bracket of FIG. 1.

FIG. 1 illustrates a self-ligating bracket B similar to that disclosed in U.S. Pat. No. 6,368,105, which is incorporated herein in its entirety. More specifically, the bracket B includes a base 10 and a locking member 12 slidable relative to the base 10. The base 10 includes a series of dove tail undercuts 14 that facilitates bonding of the base 10 to a tooth.

The base 10 further includes a lingual slot 16 that at least partially defines a gingival-occlusal opening 18 adapted to receive and guide the locking member 12 (as shown in phantom in FIG. 1). The slot 16 is preferably machined into the lingual surface 20 of the base 10 after creation of the base 10. The slot 16 may be formed by cutting (e.g., by a machine or laser) or by burring. However, as an alternative, the slot 16 may be formed (e.g., molded) during creation of the base 10.

An insert 22 is secured to the lingual surface 20 of the base 10 in order to at least partially define the gingival-occlusal opening 18. In the embodiment illustrated in FIGS. 5, the insert 22 is a channel having a C-shaped cross section. The open side of the channel is positioned to face the lingual surface 20 of the base 10 so that the insert 22 and the base 10 will cooperatively define the gingival-occlusal opening 18.

Figure 5:
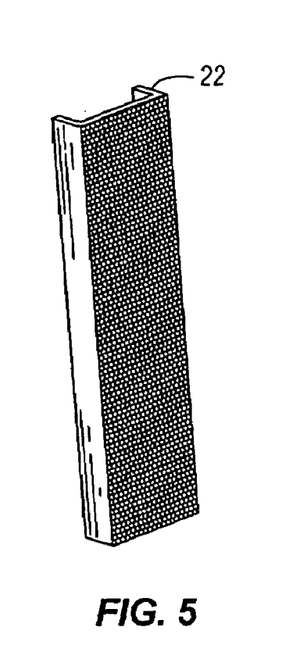
FIG. 5 illustrates the insert of FIG. 1.

The insert 22 can be secured to the base 10 by any appropriate process, such as bonding agent, pressed fit, mechanical interlock, brazing, etc. The insert 22 can be made of metal or a combination of metals (e.g., stainless steel, silver-gold, gold-palladium, gold, silver, etc.) resin, silicate, glass, marble, ceramic, granite, or other suitable material.

Figure 3:
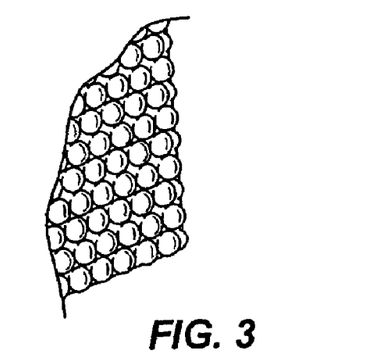
FIG. 3 is an enlarged view of a lingual surface of an insert of FIG. 2.
Figure 6:
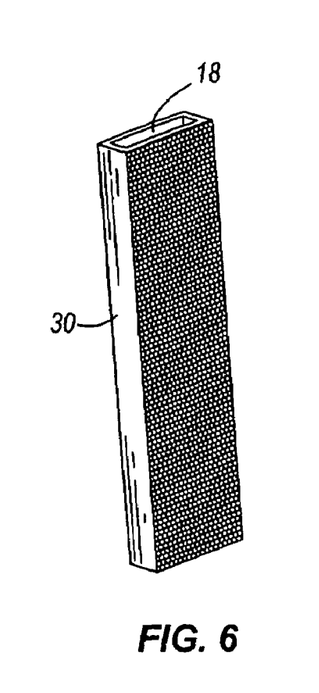
FIG. 6 illustrates an alternative insert that can be used to practice the present invention.
Figure 7:
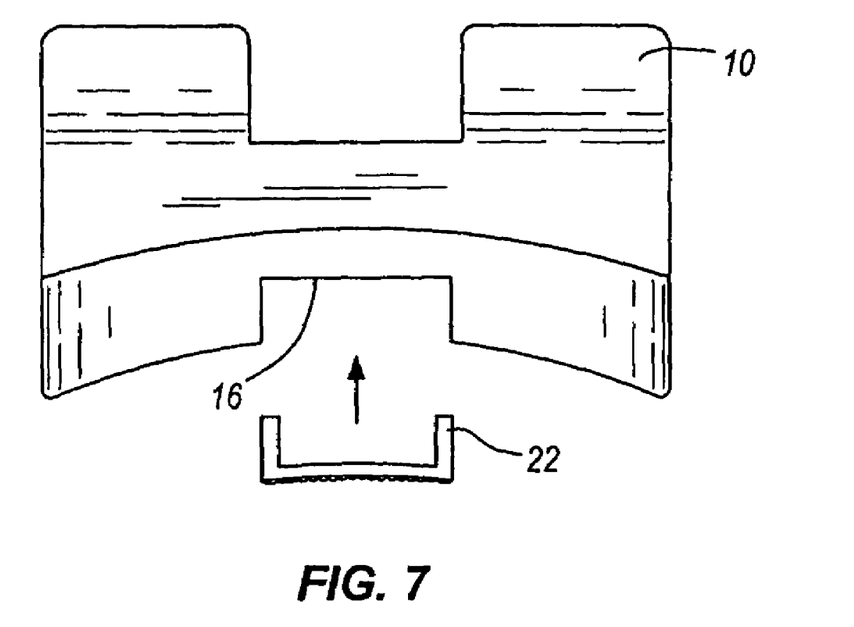
FIG. 7 illustrates a gingival view or an end view of the bracket of FIG. 2.

FIG. 6 illustrates and alternative configuration for an insert 30. In this embodiment, the insert 30 has a closed cross section in the form of a rectangle. In the embodiment of FIG. 3, it can be seen that the insert 30 fully defines the gingival-occlusal opening 18. It should be understood that, in other constructions (not shown), the slot 16 may be provided by the base 14 without a separate insert (such as insert 22 or 30).

In either of the above-referenced embodiments, the insert 22 or 30 may be coated on the lingual surface with a resin in order to achieve a desired color, durability, and adhesion between the tooth enamel and the insert. As a further alternative, silane may be used on the lingual surface of the insert 22 or 30 for additional adhesion to the enamel.

In addition, the exterior or lingual surface of the insert 22 may include projecting surface portions, retrusive undercuts, or mesh (e.g., metal mesh) and define associated recessed surface portions to provide a non-smooth configuration. The lingual surface of the insert 22 is preferably scored, micro-abraded (FIGS. 1 and 4), micro-etched (chemically or with laser-etching) or may contain micro-protrusions (FIGS. 2–3 and 5–6). These surface treatments of the insert produce micro-undercuts to permit a stronger bonding surface for the bonding resin that is sandwiched between the treated lingual surface of the insert 22 (and ceramic base 10) and the enamel of the tooth surface. This maximizes bond strength to prevent debonding of the entire bracket B from the tooth. It should be understood that, in other constructions (not shown), the lingual surface of the insert 22 may be substantially smooth.

Figure 4:
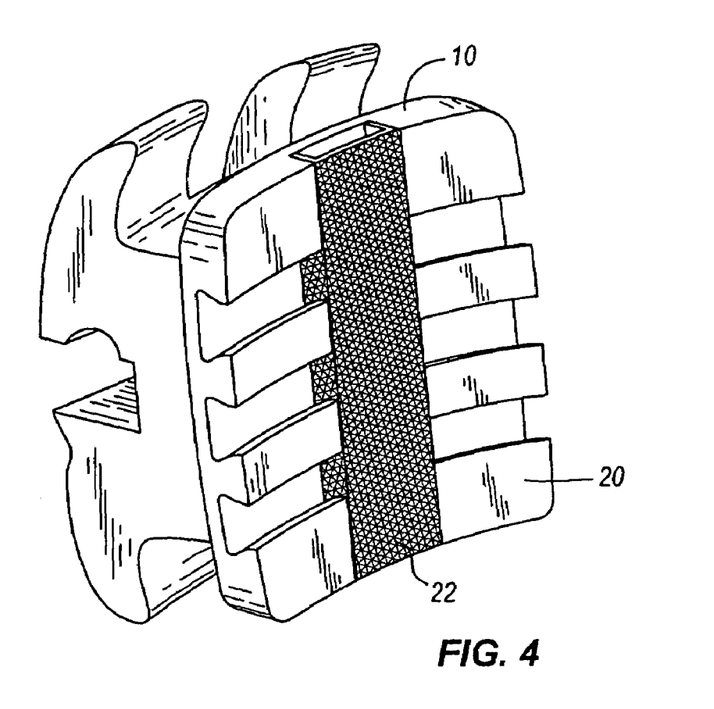
FIG. 4 illustrates a lingual perspective view of the bracket of FIG. 1 fully assembled.
Figure 8:
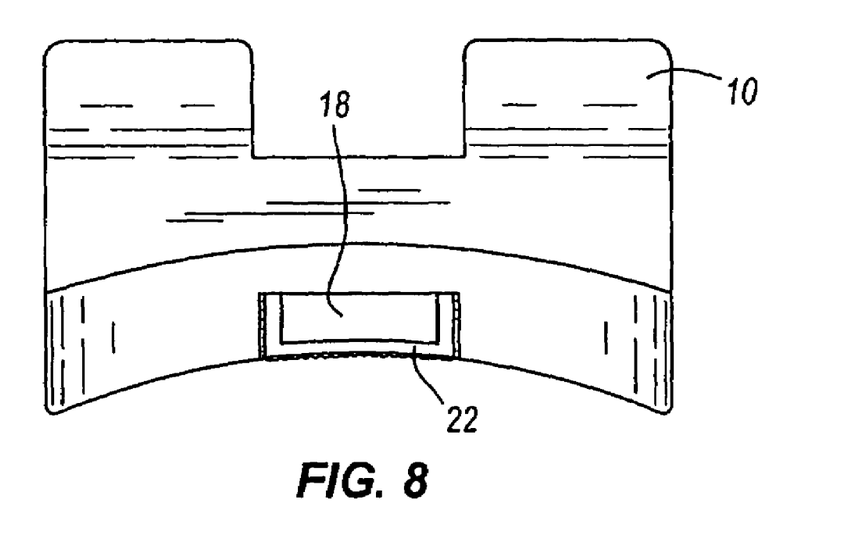
FIG. 8 illustrates a gingival view or an end view of the bracket of FIG. 4 in the assembled condition.

As shown in FIGS. 4 and 8, when the insert 22 is secured in the slot 16, it is desired that the insert 22 will be flush with the lingual surface 20 of the base 10. If desired, the lingual portion 32 of the insert 22 can be slightly concave (see FIG. 8) to match the contour of the lingual surface 20 of the base 10. Such a design facilitates bonding the bracket B to a curved surface of a tooth.

Figure 9:
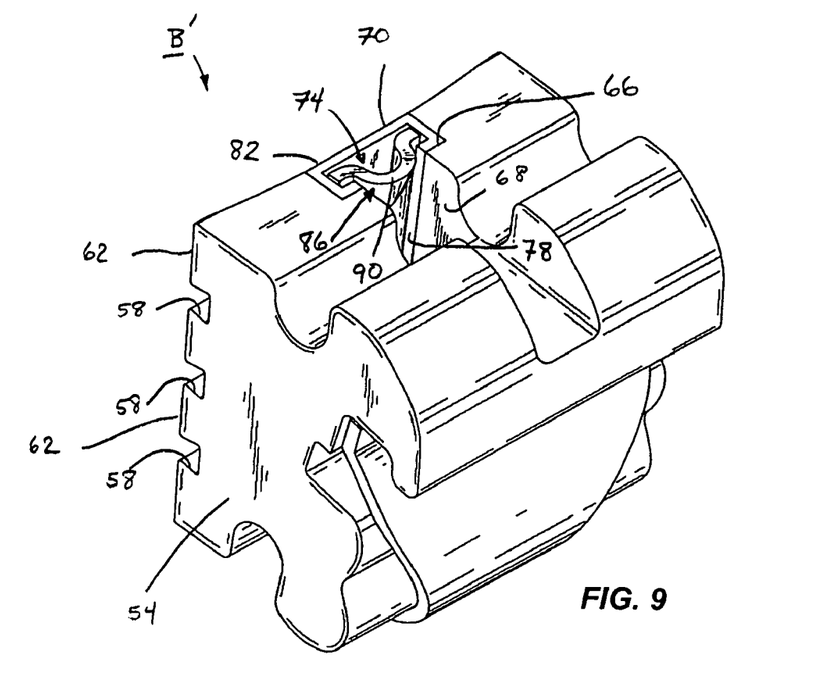
FIG. 9 is a top perspective view of an orthodontic bracket assembly according to another embodiment of the present invention.

FIG. 9 illustrates a self-ligating bracket B' similar to the bracket B described above. More specifically, the bracket B' includes a base 54. The base 54 includes a series of dove-tail undercuts 58 that facilitate bonding of a lingual surface 62 to a tooth.

Figure 11:
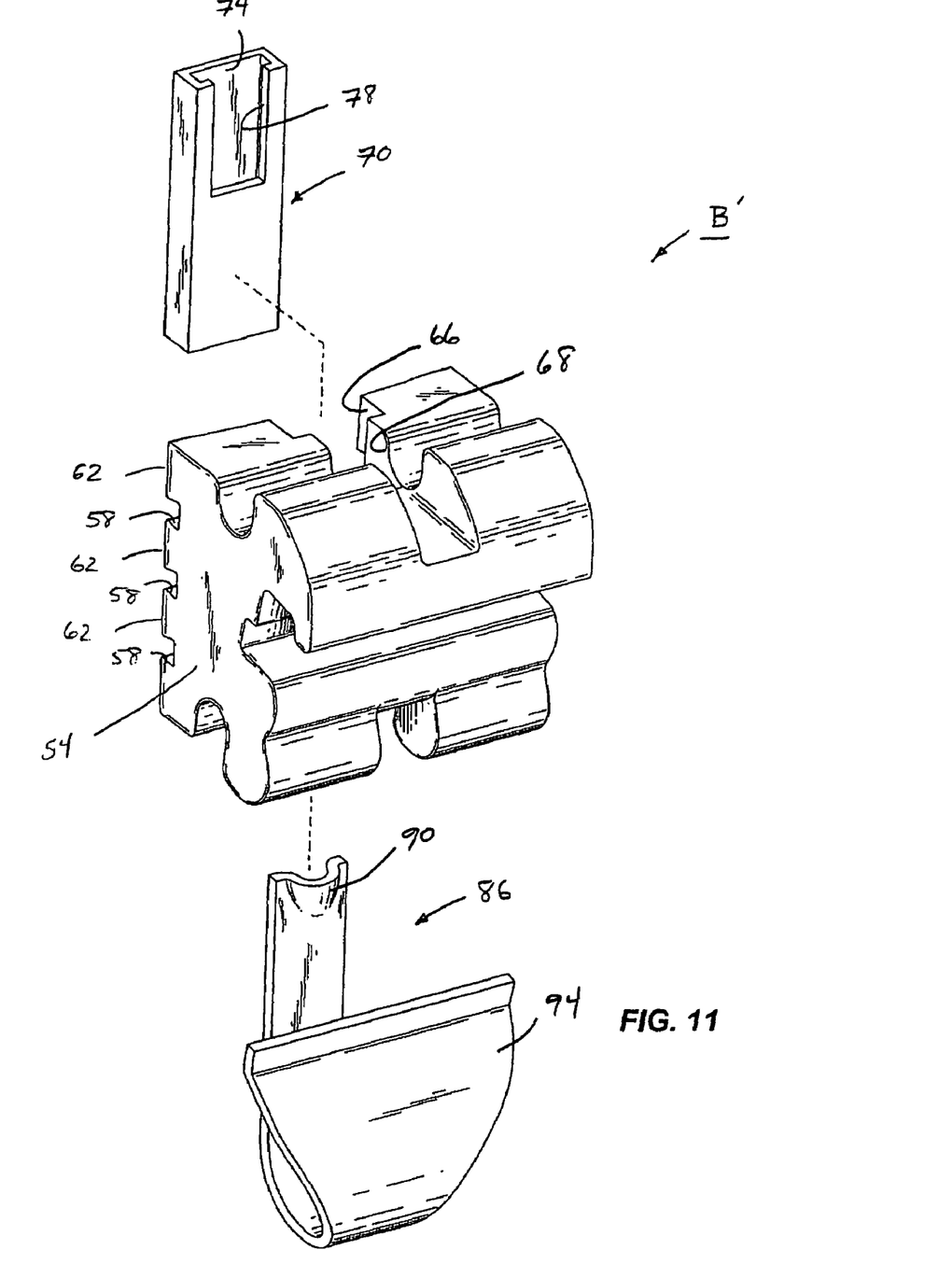
FIG. 11 is an exploded view of the orthodontic bracket assembly of FIG. 9.

The base 54 further includes a slot 66 (shown in FIG. 11) that is preferably machined into the lingual surface 62 of the base 54 after creation of the base 54. However, as an alternative, the slot 66 may be formed (e.g., molded) during creation of the base 54. The slot 66 is open to a cut-out 68 in the base 54. The slot 66 may be adapted to receive an insert 70.

The insert 70 is secured to the lingual surface 62 of the base 54. In the independent embodiment illustrated in FIGS. 9–13, the insert 70 is rectangular with a slot 74 extending through the length of the insert 70. The insert 70 also includes an aperture 78 (shown in FIG. 11) that faces away from the lingual surface 62 of the base 54.

The insert 70 can be secured to the base 54 by any appropriate process, such as bonding, pressed fit, mechanical interlock, welding, etc. The insert 70 can be made of metal or a combination of metals (e.g., stainless steel, silver-gold, gold-palladium, gold, silver, etc.) resin, silicate, glass, marble, ceramic, granite, or other suitable material.

The insert 70 has a lingual surface 82 that, when inserted in the base 54, aids in securing the base 54 to the tooth. When the insert 70 of the independent embodiment illustrated in FIGS. 9–13 is positioned inside of the slot 66 of the base 54, the slot 74 of the insert 70 is aligned with slot 66 and shares a longitudinal axis. The slot 74 of the insert 70 is aligned inside of the slot 66 of the base 54 to receive a locking member 86 when the insert 70 is secured to the base 54.

Figure 13:
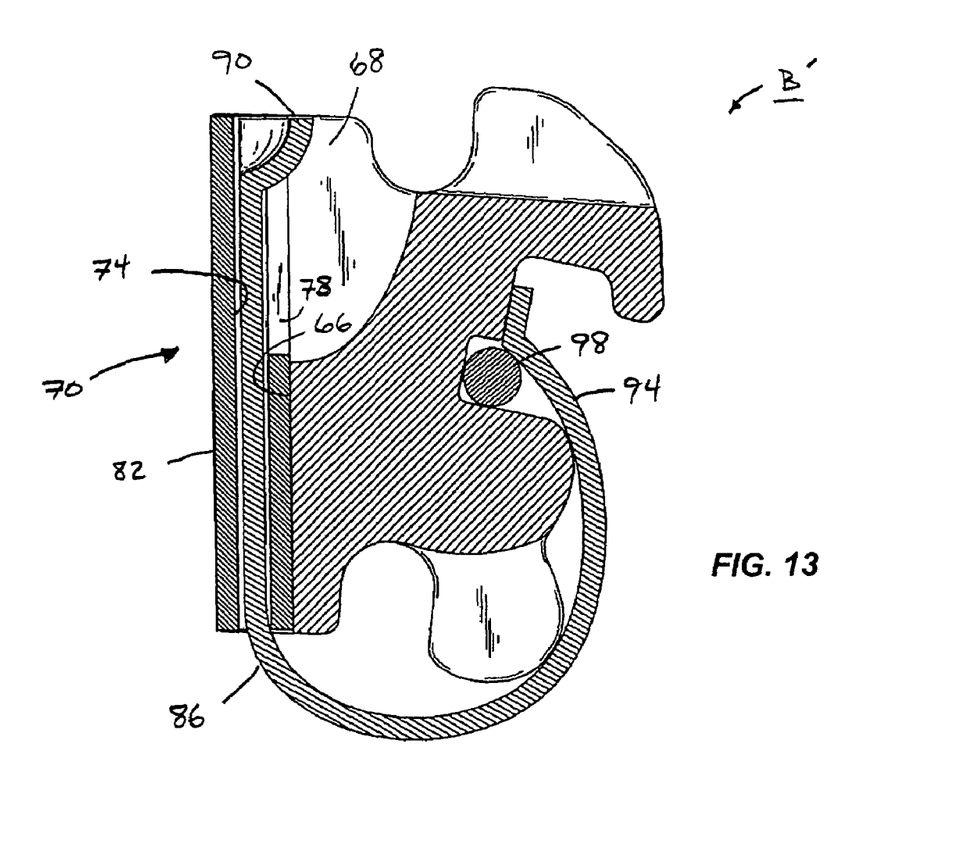
FIG. 13 is a cross-section view of the orthodontic bracket assembly of FIG. 9 taken along line 13—13.

As shown in FIG. 13, the locking member 86 has a rounded portion 90 for receiving a tool to move the locking member 86 from a closed position (FIG. 13) to an open position. A buccal portion 94 of the locking member holds a wire 98 within the base 54. By inserting a tool (not shown) into the rounded portion 90, the locking member 86 can be pushed downward within the slot 74 to the open position in which the wire 98 is exposed for removal or insertion of a new wire. The cut-out 68 in the base 54 allows for the tool and rounded portion 90 of the locking member 86 to move partially into the cut-out 62 to disengage the locking member 86 from the insert 70 and allow the locking member 86 to slide downward within the slot 74 of the insert 70.

In addition, the exterior or lingual surface 82 of the insert 70 is preferably scored, micro-abraded, micro-etched (chemically or with laser-etching) or may contain micro-protrusions. These surface treatments of the insert 70 produce micro-undercuts to permit a stronger bonding surface for the bonding resin that is sandwiched between the treated lingual surface 82 of the insert 70 (and ceramic base 54) and the enamel of the tooth surface. This maximizes bond strength to prevent debonding of the entire bracket B' from the tooth.

Figure 10:
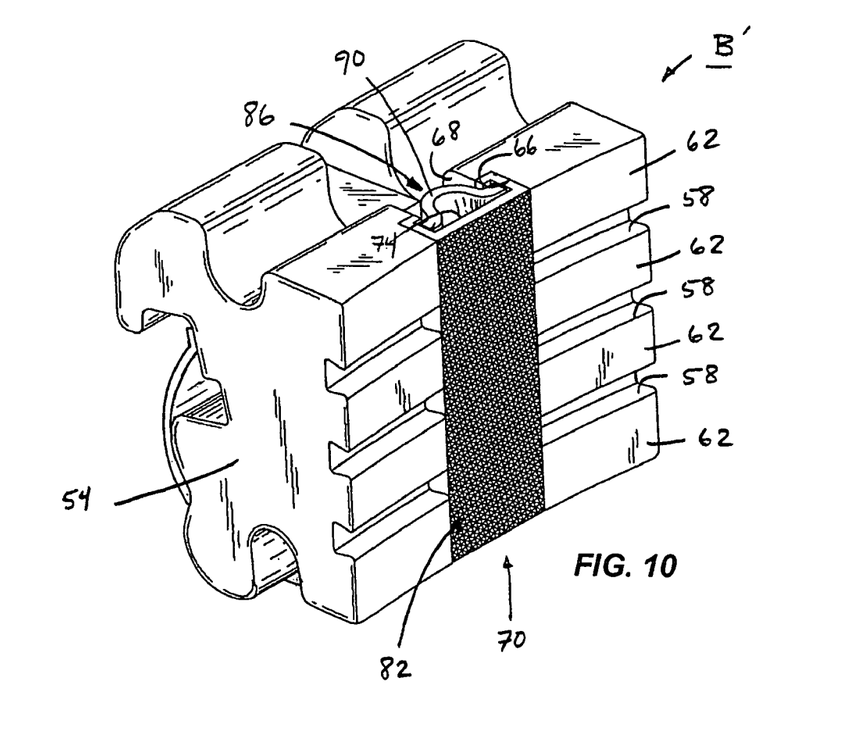
FIG. 10 is a rear perspective view of the orthodontic bracket assembly of FIG. 9.
Figure 12:
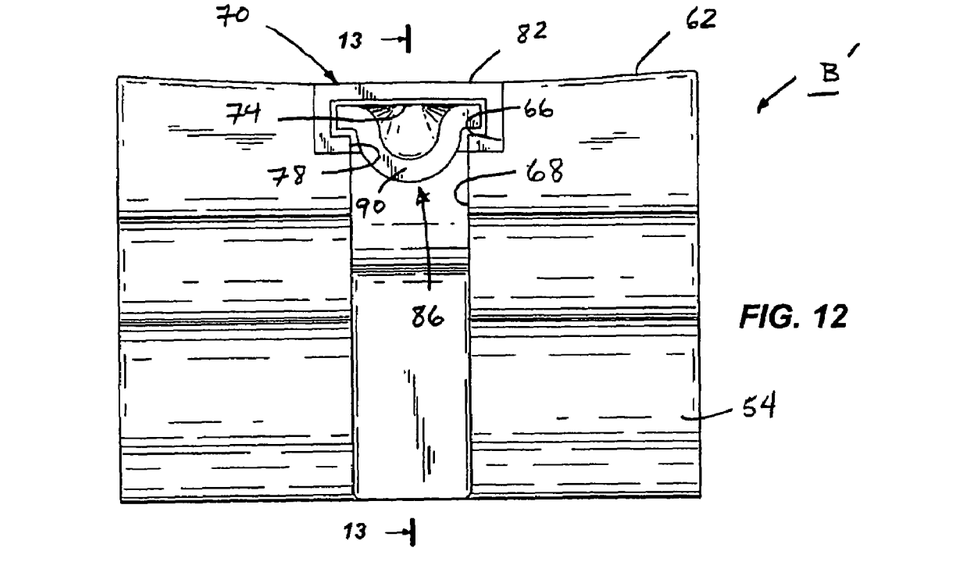
FIG. 12 is a top view of the orthodontic bracket assembly of FIG. 9.

As shown in FIGS. 10 and 12, when the insert 70 is secured in the slot 66, it is desired that the insert 70 will be flush with the lingual surface 62 of the base 54. If desired, the lingual surface 82 of the insert 70 can be slightly concave to match the contour of the lingual surface 62 of the base 54. Such a design facilitates bonding the bracket B' to a curved surface of a tooth.

Figure 14:
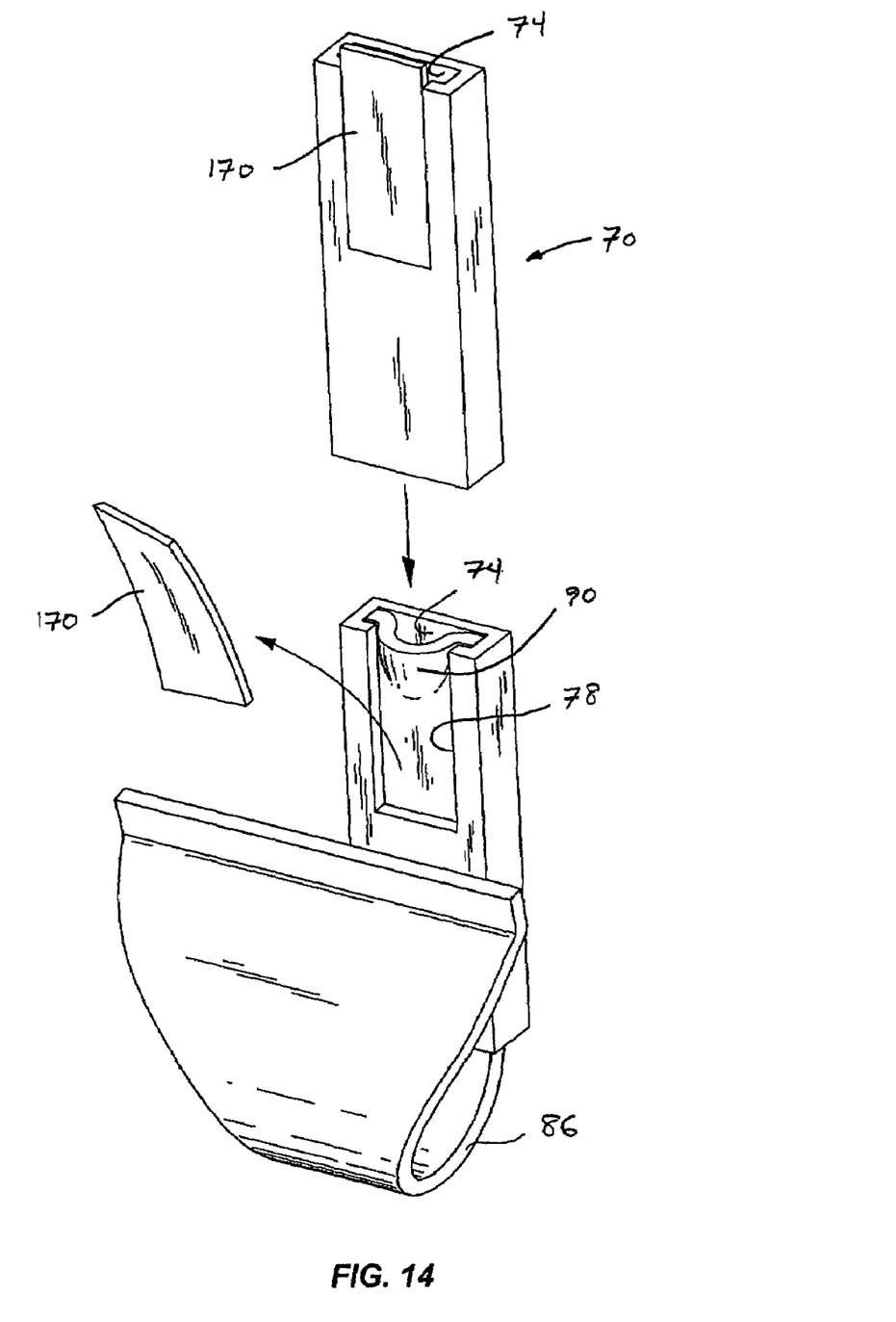
FIG. 14 illustrates a method for assembling a portion of the orthodontic bracket assembly of FIG. 13.

FIG. 14 illustrates a method for attaching the insert 70 into the body 54. The insert 70 includes a tab 170 that can be relatively flexible. Because the locking member 86 includes a rounded portion 90 for use with a tool, the flexibility of the tab 170 allows for easier insertion of the locking member 86 with a rounded portion 90 into the slot 74 of the insert 70.

The tab 170 helps to prevent bonding substances from entering the lingual slot 74 when the insert 70 is fastened to the base 54. The tab 170 generally remains on the insert 70 until the locking member 86 is inserted, but can be removed before the locking member 86 is inserted into the slot 74. After removal of the tab 170, the insert 70 yields an aperture 78 such that the rounded portion 90 of the locking member 86 can be engaged with a tool to move the locking member 86 to the open position.

Figure 15:
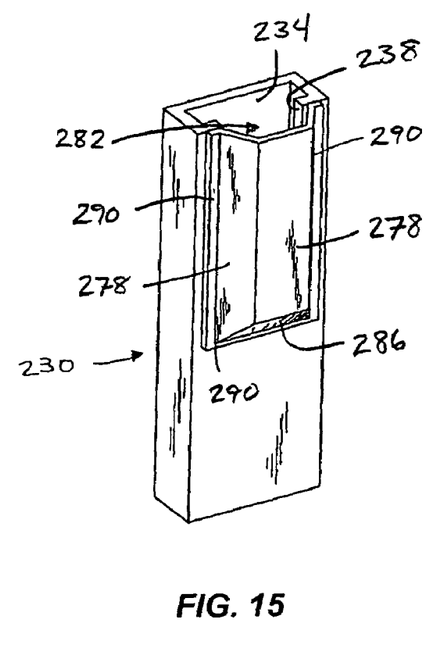
FIG. 15 is a perspective view of an insert for an orthodontic bracket according to a further embodiment of the present invention.
Figure 16:
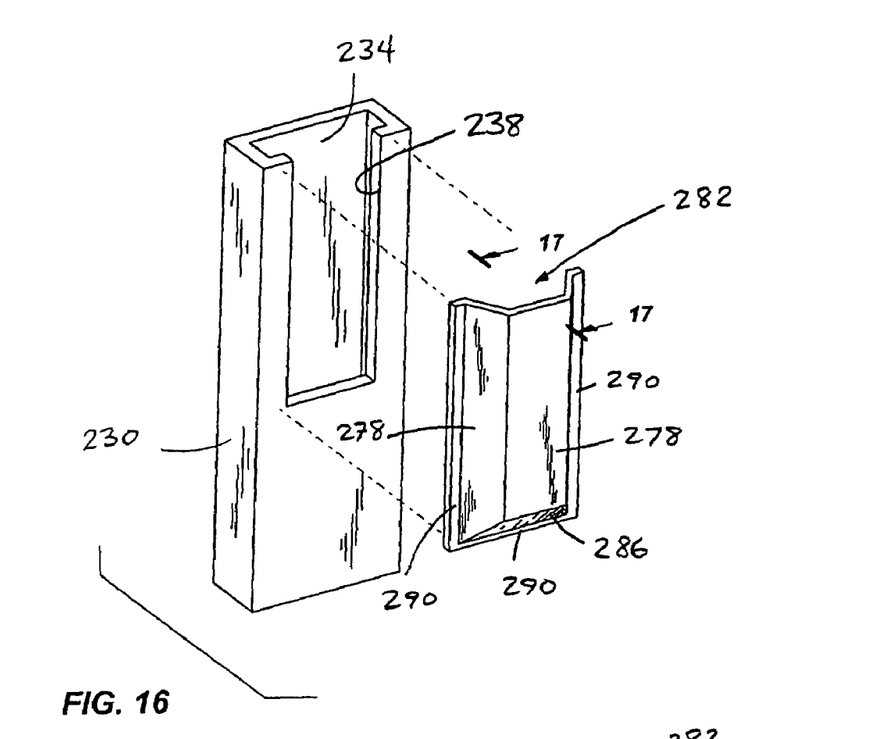
FIG. 16 is an exploded view of the insert of FIG. 15.
Figure 17:
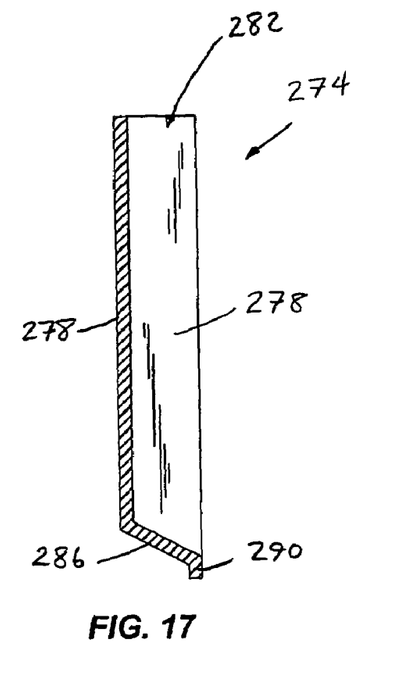
FIG. 17 is a cross-section view of a portion of the insert of FIG. 15 taken along line 17—17 in FIG. 16.

A third embodiment of the invention is illustrated in FIGS. 15–17. An insert 230 is shown for use with the base 54 or similar base including a slot 66 and a cut-out 68. The insert 230, similar to insert 70 shown in FIGS. 9–13, includes a slot 234 and an aperture 238.

In the embodiment shown in FIGS. 15–17, an aperture cover 274 includes three sides 278, an open top 282, a bottom panel 286, and a fastening portion 290. The fastening portion 290 extends about the sides 278 and the bottom panel 286. In other independent embodiments, the aperture cover 274 can have more or less sides, be rounded to form a concave surface about the aperture 238, or comprise a plurality of different styles. The aperture cover 274 can be integrally molded with the insert 230 or can be fastened to the insert 230 prior to affixing the insert 230 to the base 54.

The aperture cover 274 protects the inside of the slot 234 from bonding substances that may enter when the insert 230 is fastened to the base 54. A locking member (not shown), similar to the locking member 86 shown in FIGS. 9–13 can be inserted into the slot 234 prior to or after the insert 230 is fastened to the base 54. The open top 282 of the aperture cover 274 allows the tool to be inserted into a rounded portion similar to the rounded portion 90 (shown in FIGS. 9–13) of the locking member to move the locking member to a second position (e.g., an open position) partially engaged with the base 54.

Figure 18:
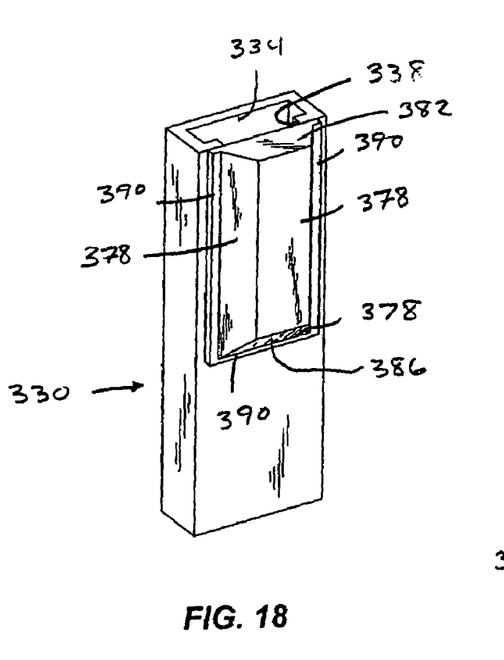
FIG. 18 is a perspective view of an insert for an orthodontic bracket according to another embodiment of the present invention.
Figure 19:
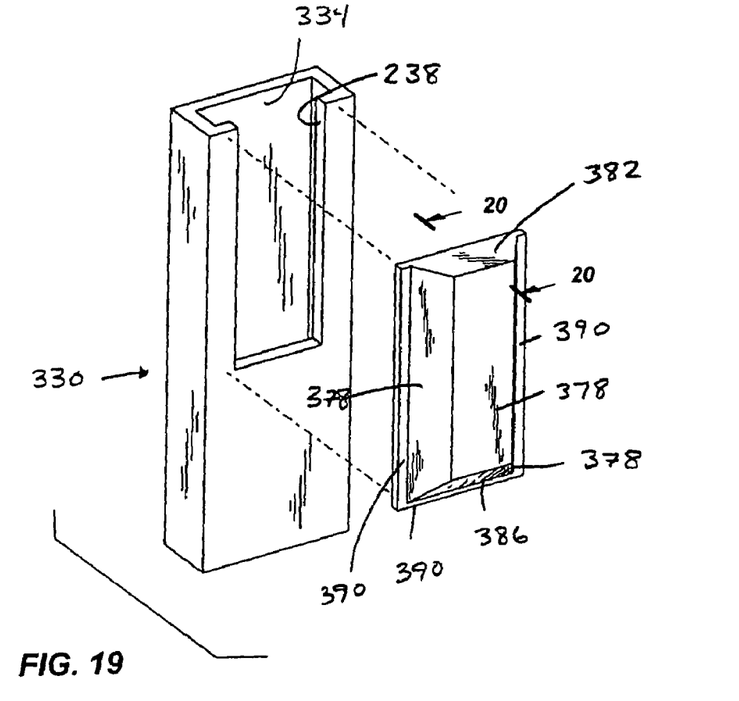
FIG. 19 is an exploded view of the insert of FIG. 18.
Figure 20:
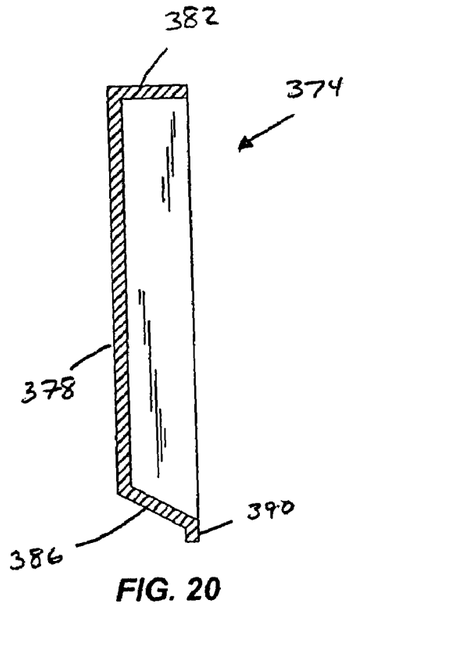
FIG. 20 is a cross-section view of a portion of the insert of FIG. 18 taken along line 20—20 in FIG. 19.

A fourth embodiment of the invention is illustrated in FIGS. 18–20. An insert 330 is shown for use with the base 54 or similar base including a slot 66 and a cut-out 68. The insert 330, similar to insert 70 shown in FIGS. 9–13, includes a slot 334 and an aperture 338.

In the embodiment shown in FIGS. 18–20, an aperture cover 374 includes three sides 378, a top panel 382, a bottom panel 386, and a fastening portion 390. The fastening portion 390 extends about the sides 378 and the bottom panel 386. In other independent embodiments, the aperture cover 374 can have more or less sides, be rounded to form a concave surface about the aperture 338, or comprise a plurality of different styles. The aperture cover 374 can be integrally molded with the insert 330 or can be fastened to the insert 330 prior to affixing the insert 330 to the base 54.

The aperture cover 374 protects the inside of the slot 334 from bonding substances that may enter when the insert 330 is fastened to the base 54. A locking member (not shown), similar to the locking member 86 shown in FIGS. 9–13 can be inserted into the slot 334 prior to or after the insert 330 is fastened to the base 54. The open top of the slot 334 of the insert 330 allows the tool to be inserted into a rounded portion similar to the rounded portion 90 (shown in FIGS. 9–13) of the locking member to move the locking member to a second position (e.g., an open position) partially engaged with the base 54.

One or more independent features or independent advantages may be set forth in the following claims:

What is claimed is:

1. An orthodontic bracket assembly comprising:
   a base defining an archwire slot and having a lingual surface attachable to a tooth, the base defining a recess extending from the lingual surface;
   a locking member including a lingual portion positioned in the recess to support the locking member on the base, the lingual portion being movable in the recess between an open position, in which the locking member permits access to the archwire slot, and a closed position, in which the locking member inhibits access to the archwire slot; and
   an insert positioned in the recess, the insert including a lingual wall at least partially covering the recess, the insert and the base cooperating to define a slot, the locking member being positioned in the slot to support the locking member on the base.

2. The bracket assembly of claim 1 wherein the recess includes a slot having an open end and extending along an axis, the lingual portion being insertable through the open end and movable along the axis.

3. The bracket assembly of claim 1, wherein the lingual wall has an insert lingual surface attachable to the tooth, the insert lingual surface having a non-smooth configuration.

4. The bracket assembly of claim 3, wherein the insert lingual surface includes projecting surface portions and defines associated recessed surface portions to provide the non-smooth configuration.

5. The bracket assembly of claim 3, wherein the insert lingual surface includes one or more of projecting surface portions, retrusive undercuts, and metal mesh and defines associated recessed surface portions to provide the non-smooth configuration of the insert lingual surface.

6. The bracket assembly of claim 1, wherein the lingual wall has an insert lingual surface attachable to the tooth, the insert lingual surface being substantially smooth.

7. The bracket assembly of claim 1, wherein the lingual wall has an insert lingual surface attachable to the tooth, and wherein the insert lingual surface is substantially flush with adjacent portions of the lingual surface of the base.

8. The bracket assembly of claim 7, wherein the lingual wall of the insert has a concave shape to facilitate attachment to a tooth.

9. The bracket assembly of claim 1, wherein the insert has a substantially C-shaped cross-section.

10. The bracket assembly of claim 1, wherein the insert further includes a labial wall spaced from the lingual wall such that the insert defines the slot, the locking member being positioned in the slot to support the locking member on the base.

11. The bracket assembly of claim 10, wherein the labial wall defines an aperture, wherein the base defines an opening communicating with the recess and extending away from the lingual surface, the aperture being at least partially alignable with the opening.

12. The bracket assembly of claim 11, wherein the lingual portion of the locking member includes a first portion and a second portion extending labially of the first portion, the second portion projecting into the aperture.

13. The bracket assembly of claim 11, wherein the insert further includes a cover portion at least partially covering the aperture.

14. The bracket assembly of claim 13, wherein the insert is bonded to the base with a bonding substance, the cover portion inhibiting bonding substance from entering the slot.

15. The bracket assembly of claim 1, wherein the base defines an opening communicating with the recess and extending away from the lingual surface, and wherein the lingual portion of the locking member includes a first portion and a second portion extending labially of the first portion, the second portion projecting into the opening.

16. A method of assembling an orthodontic bracket assembly, the bracket assembly including a base defining an archwire slot and having a lingual surface attachable to a tooth, an insert, and a locking member including a lingual portion, the method comprising the acts of:

defining a recess in the lingual surface;

securing the insert in the recess to thereby define a slot; and positioning the lingual portion of the locking member in the slot to support the locking member on the base such that the lingual portion is movable in the slot between an open position, in which the locking member permits access to the archwire slot and a closed position, in which the locking member inhibits access to the archwire slot.

17. The method of claim 16, wherein defining a recess includes machining the recess into the base.

18. The method of claim 16, wherein the insert has an insert lingual surface, and wherein securing includes positioning the insert with the insert lingual surface substantially flush with adjacent portions of the lingual surface of the base.

19. The method of claim 16, wherein the insert further includes a labial wall spaced from the lingual wall, wherein labial wall defines an aperture, wherein the lingual portion of the insert includes a first flat portion and a second portion extending labially of the flat portion, and wherein positioning includes positioning the lingual portion of the locking member in the slot with the second portion projecting into the aperture.

20. The method of claim 19, and further comprising, before positioning, at least partially covering the aperture with a cover portion.

21. The method of claim 20, wherein securing the insert includes bonding the insert in the recess with bonding substance, and wherein covering includes inhibiting bonding substance from entering the slot.

22. The method of claim 21, and further comprising, after securing, removing the cover portion.

23. An orthodontic bracket assembly comprising:

a base defining an archwire slot and having a lingual surface attachable to a tooth, the base defining a recess extending from the lingual surface;

an insert secured in the recess, a slot being at least partially defined by the insert, the insert having an insert lingual surface attachable to the tooth, the insert lingual surface having a non-smooth configuration, the insert lingual surface being substantially flush with adjacent portions of the lingual surface of the base and having a concave shape to facilitate attachment to a tooth; and a locking member including a lingual portion positioned in the slot to support the locking member on the base, the lingual portion being movable in the slot between an open position, in which the locking member permits access to the archwire slot, and a closed position, in which the locking member inhibits access to the archwire slot.

* * * * *